United States Patent [19]

Giersch et al.

[11] Patent Number: 4,818,747
[45] Date of Patent: Apr. 4, 1989

[54] BICYCLIC ALIPHATIC ALCOHOLS AND THEIR UTILIZATION AS PERFUMING INGREDIENTS

[75] Inventors: Wolfgang K. Giersch; Günther Ohloff, both of Bernex, Switzerland

[73] Assignee: Firmenich SA, Geneva, Switzerland

[21] Appl. No.: 169,536

[22] Filed: Mar. 17, 1988

[30] Foreign Application Priority Data

Mar. 17, 1987 [CH] Switzerland ............... 1006/87-5

[51] Int. Cl.$^4$ .............................................. A61K 7/46
[52] U.S. Cl. ............................................ 512/14; 512/8; 512/25; 568/816; 568/819
[58] Field of Search ............... 568/816, 819; 512/14, 512/25, 8

[56] References Cited

U.S. PATENT DOCUMENTS 4,163,866  8/1979  Strickler .................. 568/819

FOREIGN PATENT DOCUMENTS 529082  11/1972  Switzerland ................. 568/819

Primary Examiner—Werren B. Lone
Attorney, Agent, or Firm—Pennie & Edmonds

[57] ABSTRACT

Bicyclic aliphatic alcohols or formula

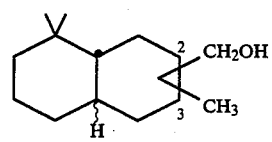

(I)

wherein substituents $CH_2OH$ and $CH_3$ are geminally bound to the carbon atom in position 2 or 3 of the hexanic ring and wherein the wavy line stands for a C-H bond of cis or trans configuration. Use of same as perfuming ingredients.

12 Claims, No Drawings

BICYCLIC ALIPHATIC ALCOHOLS AND THEIR UTILIZATION AS PERFUMING INGREDIENTS

BRIEF SUMMARY OF THE INVENTION

The instant invention relates to bicyclic aliphatic alcohols of general formula

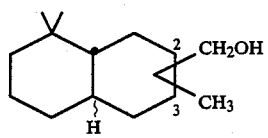

(I)

wherein substituents CH₂OH and CH₃ are geminally bound to the carbon atom in position 2 or 3 of the hexanic ring and wherein the wavy line stands for a C-H bond of cis or trans configuration.

The invention provides further a process for the preparation of the said alcohols of formula (I), which process is characterized by the following reaction step:

a. ethyl methacrylate is added to myrcene under the conditions of a Diels-Alder type reaction and the resulting reaction mixture is treated with an acidic cyclisation catalyst;
b. the obtained ester is reduced by catalytic hydrogenation, and
c. the resulting product is finally reduced by means of a usual reduction reagent of the ester function.

A further object of the present invention is a process to confer, modify or enhance the odor properties of perfumes, perfume bases or perfumed products, which process consists in adding to said perfume, perfume bases or perfumed products an odor effective amount of a bicyclic aliphatic alcohol of formula (I).

THE INVENTION

The instant invention relates to the field of perfumery, and more particularly, it relates to the utilization of bicyclic aliphatic alcohols as perfuming ingredients for the preparation of perfumes, perfume bases and perfumed products.

Among the varieties of compounds of current use in perfumery, numerous are those destined to confer an odor character of woody type to compositions or products wherein they are incorporated. Nontheless, the perfumer is often confronted with the need to employ various ingredients possessing, for the same type of fundamental odor note, specific nuances often original and unprecedented.

We have now discovered that bicyclic alcohols of general formula

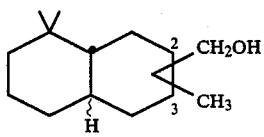

(I)

wherein substituents CH₂OH and CH₃ are geminally bound to the carbon atom in position 2 or 3 of the hexanic ring and wherein the wavy line stands for a C-H bond of cis or trans configuration, were able to confer, modify or enhance the odor properties of perfumes, perfume bases and perfumed products while developing a well-pronounced amber-like note.

The alcohols of the present invention possess in fact a natural woody odor with an ambery character. The woody note is reminiscent in particular of cedar wood without however possessing the "sawdust" character of this latter. The ambery note, on the other hand, is reminiscent of certain aspects presented by precious materials such as grey amber or AMBROX (registered trademark of Firmenich SA). The alcohols of the invention possess also a sweet, almost lactonic nuance which harmoniously rounds off the ambery note.

Owing to their odor properties, the alcohols of the invention find a utilization of wide scope, both in alcoholic perfumery and in technical applications such as, for example, in the perfuming of soaps, powder or liquid detergents, fabric softeners, household materials, cosmetics, shampoos, beauty creams, body deodorizers or airfresheners.

The proportion at which the compounds of the invention can develop the desired odorous properties can vary within a wide range of values. Typically, preferred concentrations are of between 1 and 20-25%, parts by weight. These values can be lower in the perfuming of soaps, detergents, cosmetics or the like wherein alcohols (I) are incorporated in concentrations of about 0.2-1%.

As it is often the case in perfumery, it is difficult in practice to evaluate the exact quantity required for the use of the active alcohols (I). This depends on the specific odorous effects it is desired to achieve and the nature of the products in which they are incorporated and that of the coingredients with which they are combined in a given composition.

The perfuming techniques usual in the art can also be employed in the case under examination. Thus, they can be added either directly as such to the materials it is desired to perfume or, more often, in the form of solution in admixture with other current perfume ingredients, diluents or carriers. For instance, one can mention to this effect the natural and synthetic compounds described in European patent application published under the No. 0096243 or in S. Arctander, Perfume and Flavor Chemicals, Montclair, N.J., USA (1969).

Formula (I) is deemed to define indifferently perhydro-2,5,5-trimethyl-2-naphthalene-methanol or perhydro-2,8,8-trimethyl-2-naphthalene-methanol of formula

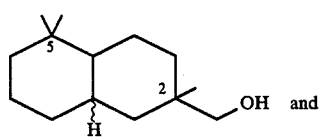 and

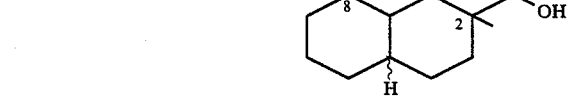

respectively. The wavy line stands for a C-H bond of cis or trans configuration.

The alcohols of the invention are new chemical entities. They are prepared according to an original process starting from mycrene according to the following reaction scheme:

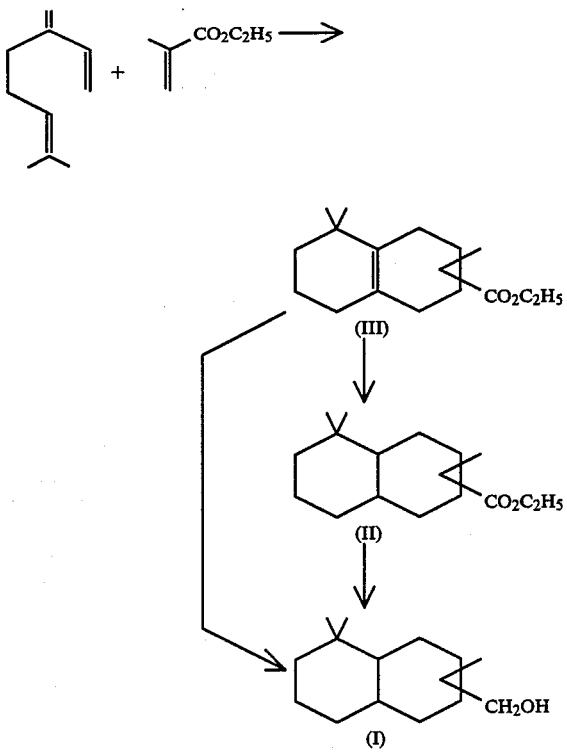

The first step of the process is characterized by a Diels-Alder type reaction between myrcene and ethyl methacrylate, followed by the cyclisation of the obtained addition product by means of an acidic cyclisation agent. Thus, after treating the mixture of myrcene/ethyl methacrylate at elevated temperature (120°–170° C.) in an inert organic solvent, the reaction mixture is treated with a Lewis acid, for example with boron trifluoride, in its etherate form, to give ester (III).

Preferably, the reaction is effected in a medium consisting in an inert organic solvent selected among aliphatic or cycloaliphatic hydrocarbons. Preferred solvents include cyclohexane. According to a specific embodiment of the process of this invention, the reaction is carried out in the presence of a polymerization inhibitor and, to this end, hydroquinone is added to the selected reactants.

The following step consists in the reduction of the cyclanic double bond by catalytic hydrogenation. This is effected in the presence of one of the usual reduction catalysts and, to this effect, one can use palladium on charcoal, Raney nickel, nickel on a solid carrier, such as silica or chromium oxide, or $PtO_2$.

According to a variant of the described process, alcohols (I) can be obtained by direct reduction of esters (III) by means of a catalytic hydrogenation in the presence of specific metal catalyst. Nickel in admixture with copper chromite can be used to this effect. In this case, the reduction is carried out preferably in an apolar medium, for example consisting in an aromatic or cycloaliphatic hydrocarbon such as toluene or cyclohexane.

The last step of the process, which consists in the reduction of ester (II), can be carried out by means of current reactants. Lithium aluminum hydride is prefectly suitable to promote such a reaction. Other metal reactants such as sodium bis(2-methoxyethoxy)-aluminohydride [Vitride (registered trademark of Ethyl Corp.)] or sodium diethylaluminate (OMH) can be used.

According to the process disclosed above, a mixture of perhydro-2,5,5-trimethyl-2-naphthalene-methanol and perhydro-2,8,8-trimethyl-napthalene-methanol was obtained. Such a mixture can be used directly without previous separation of its constituents for perfumery applications. The mixture can however be subjected to a separation according to the usual techniques such as preparative vapor phase chromatography. Two isomeric alcohols are thus isolated. It has become apparent by experience that the odorous properties of the two isomers are very similar, though perhydro-2,8,8-trimethyl-2-naphthalene-methanol shows more pronounced fragrance characters, especially the isomer hving the following structure:

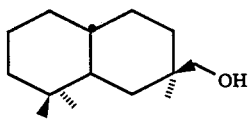

The invention is illustrated in a more detailed manner by the following examples wherein the temperatures are indicated in degrees centigrade and the abbreviations have the meaning common in the art.

EXAMPLE 1 a. In a tightly sealed vessel, a mixture consisting of 72 g of myrcene, 66 g of ethyl methacrylate, 100 g of cyclohexane and 0.2 g of hydroquinone was heated at 160° during 24 hours. The mixture was then cooled to room temperature and 10 ml of ethyl trifluoroboroetherate were added under nitrogen and with vigorous stirring. The temperature of the reaction mixture raised during the addition to about 30°, then the mixture was left to rest for 24 hours at room temperature.

The resulting mixture was then washed with two fractions of 50 ml each of 10% aqueous NaOH, then with 50 ml of water and cyclohexane was stripped off under reduced pressure. Distillation under vacuum of the residue gave 86 g of ethyl 1,2,3,4,5,6,7,8-octahydro-2,5,5(2,8,8)-trimethyl-2-naphthalenecarboxylate having b.p. 90–120°/0.1 mbar (yield: 65%).

b. 933 g of the ester obtained according to the above described process in 1000 ml of methanol were hydrogenated in the presence of 2 g of Raney nickel in an autoclave at 150° and a hydrogen pressure of 200 bar. The reaction mixture was then cooled and filtered and methanol was stripped off. The thus obtained residue was distilled under reduced pressure to give 921 g of ethyl perhydro-2,5,5(2,8,8)-trimethyl-2-naphthalenecarboxylate (yield: 98°; b.p. 81–105/0.2 mbar).

c. 920 g of the ester obtained according to the process described under letter b. above in solution in 2000 ml of toluene were added dropwise under nitrogen during 4 hours to 1850 ml of a 25% solution of sodium diethylaluminate (OMH-1 Ethyl Corp.). The mixture was left under stirring at room temperature during 2 additional hours, then it was acidified with aqueous 10% sulfuric acid. After washing with water and evaporation of toluene, there was obtained a residue which, by fractional distillation, gave 712 g of perhydro-2,5,5(2,8,8)-trimethyl-2-naphthalene-methanol (yield: 93%; b.p. 84°–90°/0.07 mbar).

EXAMPLE 2

A base composition of men Eau de Cologne was prepared by mixing the following ingredients (parts by weight):

| | |
|---|---|
| Benzyl acetate | 200 |
| Cinnamic alcohol | 50 |
| Hexylcinnamic aldehyde | 300 |
| Basilicum essential oil | 50 |
| Natural bergamote essential oil | 3500 |
| Citral | 1000 |
| Clove oil | 400 |
| Synthetic geranium oil | 100 |
| Lavander oil | 1500 |
| Methylionone[(1)] | 600 |
| Methyl dihydrojasmonate[(2)] | 1000 |
| Neroli Bigarade | 150 |
| Heliopropanal | 150 |
| Vetiver Bourbon | 100 |
| Total | 9100 |

[(1)]Iralia (registered trademark, Firmenich SA, Geneva)
[(2)]Hedione (registered trademark, Firmenich SA, Geneva)

The addition to 91 parts of the above composition of 9 parts by weight of the product obtained according to Example 1 resulted in a novel composition with a richer character and a woody-ambery note, thus rendering the base more "men-like" in character.

EXAMPLE 3

A base composition of classical chypre-type was prepared by mixing the following ingredients (parts by weight):

| | |
|---|---|
| Natural bergamote oil | 1000 |
| Sweet orange oil | 400 |
| Rose Wardia (registered trademark)[(1)] | 800 |
| 50% Oak moss[(2)] | 3800 |
| Methylionone[(3)] | 1000 |
| Synthetic amber | 1000 |
| Musk ketone | 500 |
| Total | 8500 |

[(1)]Firmenich SA, Geneva
[(2)]in dipropyleneglycol
[(3)]Iralia (registered trademark, Firmenich SA, Geneva)

The addition of 15 parts by weight of the product obtained according to Example 1 to 85 parts of the base composition described above conferred to the base a rich woody-ambery note. The sweet character of the base was modified at the same time and converted into a dry note having a more pronounced lactonic character.

EXAMPLE 4

The product obtained according to Example 1 was added at 1% to commercial soap paste of neutral odor and, according to the usual techniques, the resulting paste was used to manufacture toilet soap bars. The obtained article presented a pleasant woody, lactonic odor.

What we claim is:

1. Bicyclic aliphatic alcohols or formula

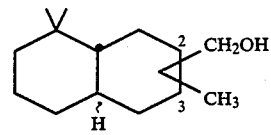

wherein substituents $CH_2OH$ and $CH_3$ are geminally bound to the carbon atom in position 2 or 3 of the hexanic ring and wherein the wavy line stands for a C-H bond of cis or trans configuration.

2. Perhydro-2,5,5-trimethyl-2-naphthalene-methanol.
3. Perhydro-2,8,8-trimethyl-2-naphthalene-methanol.
4. A process to confer, modify or enhance the odor properties of perfumes, perfume bases and perfumed products which comprises adding to said perfumes, perfume base and perfumed products an odor effective amount of a compound according to claim 1.
5. A perfume, a perfume base and a perfumed product resulting from the process of claim 4.
6. As a perfumed product according to claim 5, a solid or liquid detergent.
7. As a perfumed product according to claim 5, a fabric softener.
8. As a perfumed product according to claim 5, a soap.
9. A process for the preparation of bicyclic aliphatic alcohols according to claim 1 which comprises the following reaction steps:
   a. the addition of ethyl methacrylate to mycrene under the conditions of a Diels-Alder type reaction and the treatment of the resulting reaction mixture with an acidic cyclisation catalyst;
   b. the reduction of the obtained ester by catalytic hydrogenation, and
   c. the reduction of the resulting product by means of a usual reduction reagent of the ester function.
10. Process according to claim 9 wherein steps b. and c. are carried out simultaneously by means of a catalytic hydrogenation in the presence of a catalyst consisting of Ni-$CuCr_2O_4$.
11. Process according to claim 9 wherein the acidic cyclisation catalyst is a Lewis-type acid.
12. Process according to claim 11 wherein the Lewis-type acid is boron trifluoride.

* * * * *